(12) United States Patent
Genosar et al.

(10) Patent No.: US 6,367,471 B1
(45) Date of Patent: Apr. 9, 2002

(54) INTERNAL VORTEX MECHANISM FOR INHALER DEVICE

(75) Inventors: Amir Genosar, Pardess-Hana (IL); Richard Matthew Pavkov, Northville, MI (US)

(73) Assignee: Sheffield Pharmaceuticals, Inc., DE (US)

( * ) Notice: Subject to any disclaimer, the term of this patent is extended or adjusted under 35 U.S.C. 154(b) by 0 days.

(21) Appl. No.: 09/431,266

(22) Filed: Nov. 1, 1999

(51) Int. Cl.⁷ .............................................. A61M 11/60
(52) U.S. Cl. ............................... 128/200.23; 128/200.14
(58) Field of Search ....................... 128/200.23, 200.14, 128/200.18, 200.21, 203.12, 203.15; 239/296, 405, 489, 463

(56) References Cited

U.S. PATENT DOCUMENTS

| | | | |
|---|---|---|---|
| 2,305,210 A | * 12/1942 | Wahlin .......................... | 239/18 |
| 4,768,717 A | * 9/1988 | Shay ........................... | 239/403 |
| 5,067,655 A | * 11/1991 | Farago et al. ................ | 239/124 |
| 5,178,138 A | * 1/1993 | Walstrom et al. ......... | 128/200.23 |
| 5,228,624 A | * 7/1993 | Mensink ....................... | 239/406 |
| 5,435,297 A | * 7/1995 | Klein ....................... | 128/200.23 |
| 5,676,130 A | 10/1997 | Gupte et al. ............ | 128/203.19 |
| 5,860,416 A | * 1/1999 | Howlett ................. | 128/200.23 |
| 5,896,853 A | * 4/1999 | Howlett ................. | 128/200.23 |
| 6,026,808 A | * 2/2000 | Armer et al. .......... | 128/200.23 |
| 6,062,214 A | * 5/2000 | Howlett ................. | 128/200.23 |
| 6,095,141 A | * 8/2000 | Armer et al. .......... | 128/204.26 |

FOREIGN PATENT DOCUMENTS

| | | | | |
|---|---|---|---|---|
| EP | 0911 048 A2 | 4/1999 | | |
| GB | 2279879 A | * 1/1995 | ............ | 128/200.23 |
| WO | WO 93/00951 | 1/1993 | | |

* cited by examiner

*Primary Examiner*—John G. Weiss
*Assistant Examiner*—Teena Mitchell
(74) *Attorney, Agent, or Firm*—Fitzpatrick, Cella, Harper & Scinto

(57) ABSTRACT

A metered dose inhaler for use with a pressurized aerosol canister includes a housing defining a conduit with a mouthpiece, and an actuator with a nozzle discharge orifice arranged to discharge aerosol into the conduit. Vortex generators positioned within the wall of the conduit and in fluid communication with air inlets for receiving ambient outside air, provide the inner wall of the conduit with a circumferential-swirling turbulent boundary layer flow to minimize impaction of medication on the inner surfaces of the conduit.

13 Claims, 3 Drawing Sheets

Figure 1:
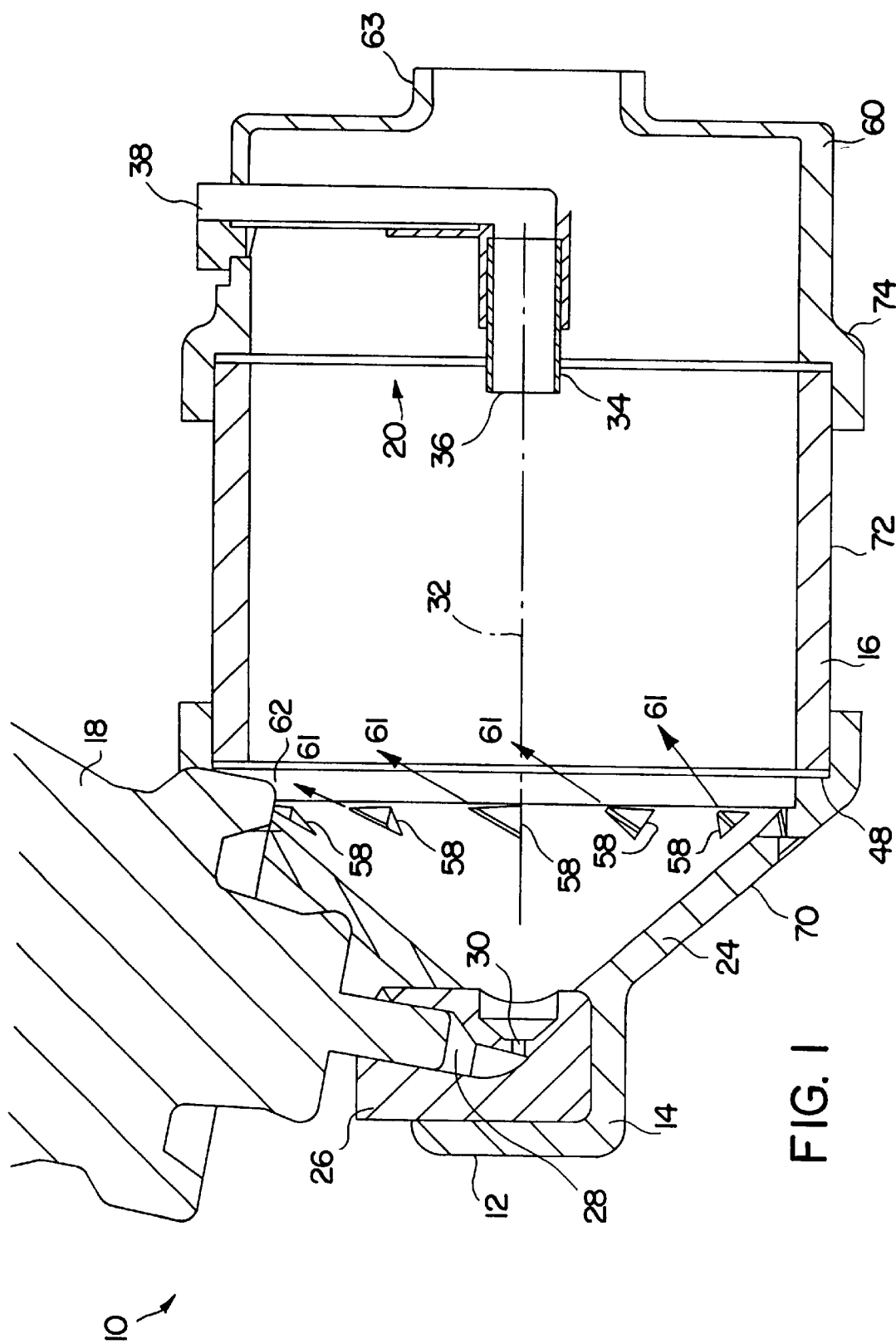
Figure 2B:
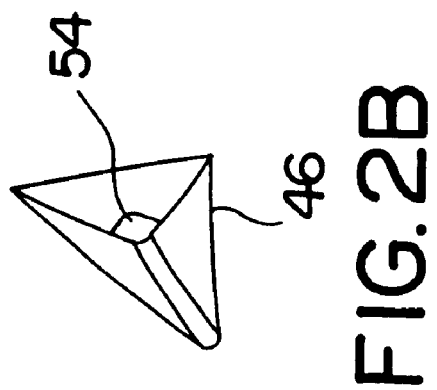
Figure 2A:
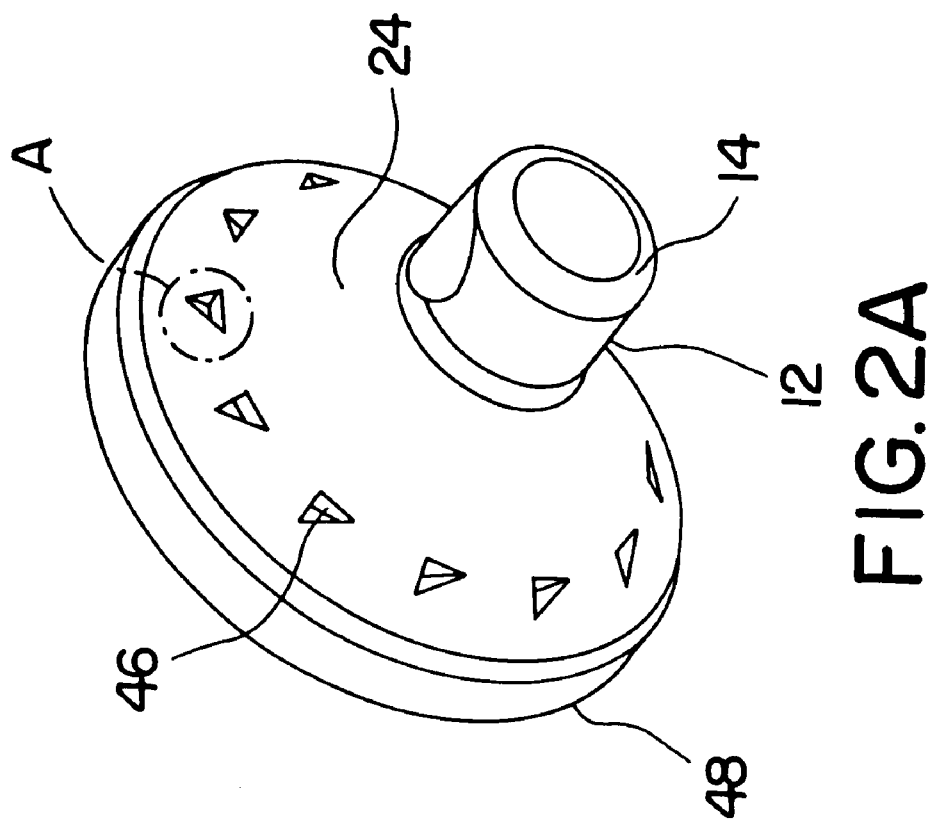

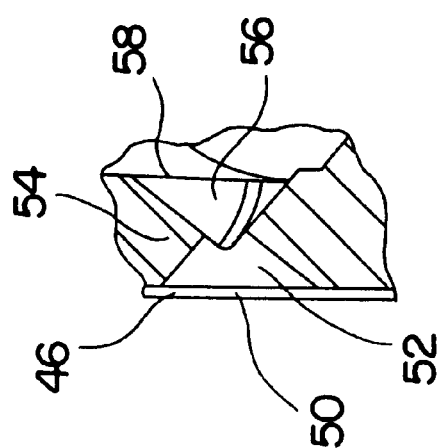
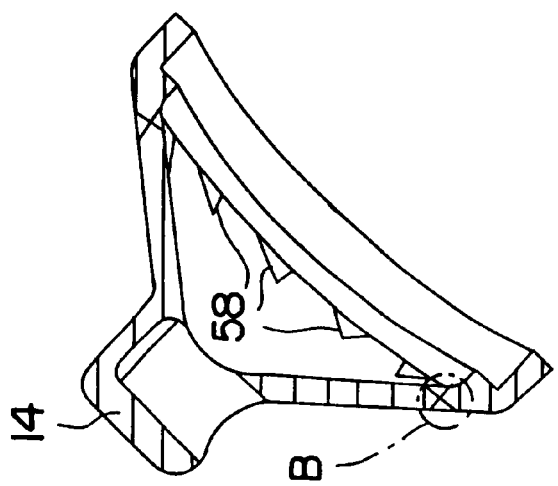
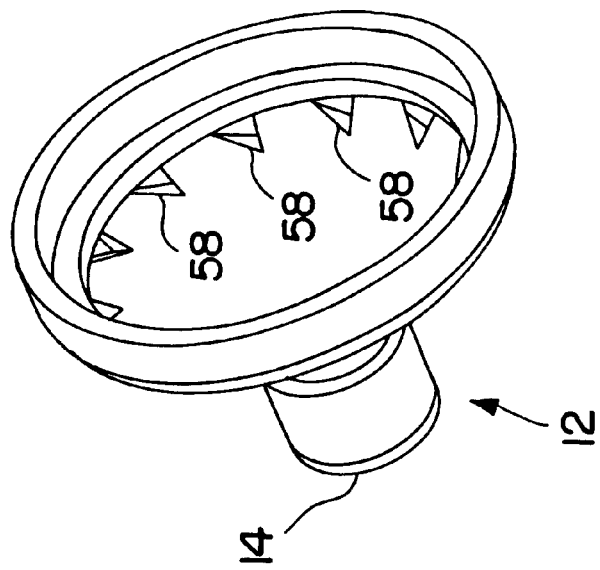

INTERNAL VORTEX MECHANISM FOR INHALER DEVICE

FIELD OF THE INVENTION

The present invention relates to methods and apparatuses for delivering a dose of aerosolized medication by inhalation into the lungs of a patient, and more particularly to an internal vortex mechanism for an inhaler device.

BACKGROUND OF THE INVENTION

Aerosols are increasingly being used for delivering medication into the lungs for therapeutic treatment of the body. For example, in the treatment of asthma, inhalers are commonly used for delivering bronchodilators such as $\beta_2$ agonists and anti-inflammatory agents such as corticosteroids. Two types of inhalers are in common use—metered dose inhalers (MDIs) and dry powder inhalers (DPIs).

In a conventional MDI device, the medication is provided by the pharmaceutical manufacturer in a pressurized aerosol canister, with the medication being suspended or dissolved in a liquid propellant such as a chloro fluorocarbon (CFC) or hydrofluoroalkane (HFA). The canister includes a metering valve having a hollow discharge stem which can be depressed inward into the canister to discharge a metered volume of propellant-medication mixture in the form of an aerosol comprising fine droplets of propellant in which particles of the medication are suspended or dissolved.

A conventional MDI for use with such a canister includes a housing having an actuator and nozzle. The canister is inserted into the housing with the hollow discharge stem of the canister being received in a bore in the actuator. Depressing the closed end of the canister causes the stem to be pushed inward into the canister so that a metered volume of medication is discharged through the nozzle. The housing further defines a flowpath in fluid communication with the nozzle, the flowpath having an outlet at a mouthpiece portion of the housing, such that the aerosolized medication may be inhaled after it exits the mouthpiece portion. The patient either inserts the mouthpiece into the mouth with the lips closed around the mouthpiece, or holds the mouthpiece at a slight distance away from an open mouth. The patient then depresses the canister to discharge the medication, and simultaneously inhales.

While generally good for many applications, existing MDIs suffer from a number of significant disadvantages. One problem with existing MDIs is poor delivery efficiency of the medication. It has been estimated that on average, with existing MDIs, only about 10 percent of the medication dose which is dispensed from the canister actually reaches the lungs where it can achieve the intended result. A significant portion of the medication impacts and sticks to the inner surfaces of the MDI device. This makes MDIs less than optimal for delivering expensive medication.

To reduce the amount of medication sticking to the inner surfaces of the MDI device, Applicants' co-pending application Ser. Nos. 08/954,352, 09/326,538, 09/326,531, disclose a series of internal vanes mounted on the inner surface of the MDI device, near the point of exit of the medication into the MDI device. Outside air is directed over the vanes during medication dispensing to create a circumferential-swirling turbulent boundary layer along the inner surface of the MDI device to minimize the impaction of medication onto the inner surfaces. Although the vanes minimize the impaction of medication, they also add to the cost and complexity of the MDI device.

Accordingly, it is an object of the present invention to provide a method and apparatus for delivering an aerosolized medication in which the respirable fraction of the metered dose (i.e., the fraction in the form of particles of the optimum size) is maximized at the exit of the apparatus.

Another object of the invention is to provide a method and apparatus for delivering an aerosolized medication in which impaction and sticking of medication on the inner walls of the apparatus is minimized.

Yet another object of the present invention is to provide an MDI device with a circumferential-swirling turbulent boundary layer of air along the inner surface of the MDI device in a cost effective and simple manner.

SUMMARY OF THE INVENTION

The above and other objects of the invention are achieved by the method and apparatuses of the invention that follow, in which flow control techniques and devices are used primarily to limit impaction and sticking of medication to the inner surfaces of an MDI device, and also aid in:

mixing ambient air with the medication and help disperse the plume of aerosolized medication;

evaporating the aerosol propellent of the medication;

directing the air/medication mixture to the mouthpiece for inhalation by a patient.

In one embodiment of the invention, an aerosol flow control apparatus includes a housing having an open end and a generally tubular conduit with a wall including an inner surface, a medication dispenser disposed within the housing and adapted to dispense a dose of aerosolized medication into the conduit, and a plurality of vortex generators formed within the wall downstream from the medication dispenser. The vortex generators establish a circumferential-swirling turbulent air flow along the inner surface upon an air flow being established through the open end.

In another embodiment of the present invention, an aerosol flow control apparatus includes a housing having a conduit defined by a wall including an inner and an outer surface, an open end adapted to be inserted into the mouth of a user and a substantially closed end remote from the open end. The apparatus also includes a medication dispenser supported in the housing and adapted to dispense a dose of aerosolized medication into the conduit, a plurality of air inlets positioned on the outer surface of the conduit, and a plurality of vortex generators positioned within the wall of the conduit downstream of the medication dispenser. The vortex generators are in fluid communication with the air inlets. An inspiratory effort exerted on the open end of the conduit causes air to flow over the vortex generators to establish a circumferential-swirling turbulent boundary layer flow along the inner surface of the conduit to reduce impaction and sticking of medication thereon.

In yet another embodiment of the present invention, a method for delivering a dose of medication in an aerosol flow control apparatus having a housing with a conduit including an inner and an outer surface, an open end adapted to be inserted into the mouth of a user, a substantially closed end remote from the open end, and a medication dispenser supported in the housing and adapted to dispense a dose of aerosolized medication into the conduit. The method includes the steps of discharging a dose of medication from the medication dispenser to form a plume of aerosolized medication within the conduit, and at least during the discharging step, providing an air flow along the inner surface of the conduit by an inspiratory effort exerted on the open end of the conduit. The air flow being drawn through a plurality of air inlets formed on the outer surface of the conduit adjacent the juncture between the conduit and the closed end of the housing and over a plurality of vortex generators formed within the wall downstream of the medication dispenser and having outlets adjacent the inner surface of the conduit. A circumferential-swirling turbulent boundary layer flow is created along the inner surface of the conduit to reduce impaction and adhesion of medication thereon.

Still another embodiment of the present invention includes an aerosol flow control apparatus having a housing including an open end and a generally tubular conduit, where the conduit includes a wall having an inner surface, and a plurality of air inlets in fluid communication with ambient air outside the conduit. The apparatus also includes a medication dispenser assembly disposed within the housing and adapted to dispense a dose of aerosolized medication into the conduit, and a plurality of vortex generators positioned within the wall of the conduit downstream of the medication dispenser. Each vortex generator includes a first generally pyramid-like portion having an apex and an open base forming an outlet located on the inner surface and a second generally pyramid-like portion having an apex and an open base in fluid communication with a corresponding air inlet. The apexes of the pyramid shaped portions overlap to form an opening allowing fluid communication between the pyramid-like portions, where the vortex generators and the air inlets cooperate to establish a circumferential-swirling turbulent air flow along the inner surface upon an air flow being established through the open end.

One of the unique features of the present invention is the decreased cost of MDI devices using the vortex generators according to the present invention, as well as the simplification of their manufacture. Specifically, the unique pyramid shapes of the vortex generators are inexpensive to produce and allow for easy fabrication/modification in plastic molding. By molding the vortex generators within the wall of the conduit, the cost of the extra material when molding vanes non the inner wall of the conduit is eliminated. In addition, the complexity of the mold for producing the conduit is decreased allowing easier manufacture of the mold and easier production of the MDI device.

The present invention results in easy manufacture using plastic injection molding, where the unique vortex generator design allows for easy pull for fabrication in plastic.

These and other objects and advantages of the present invention shall become more apparent from the accompanying drawings and the description thereof.

BRIEF DESCRIPTION OF THE DRAWINGS

The accompanying drawings, which are incorporated in and constitute a part of this specification, illustrate various embodiments of the invention and, together with the general description of the invention given above and the detailed description given below, serve to explain the principles of the invention.

FIG. 1 is a side, sectional view of the present invention.

FIG. 2A is a perspective view of the rear wall of the housing of the MDI device according to the present invention, illustrating the auxiliary air inlets and a portion of the vortex generators.

FIG. 2B is an enlarged view of an auxiliary air inlet for the MDI device according to the present invention illustrating one of the pyramid shaped portions for the vortex generators.

FIG. 3 is a perspective view of the front portion of the rear wall of the housing of the MDI device according to the present invention FIG. 4A is a side, section view of the rear wall of the housing of the MDI device according to the present invention illustrating the location of the vortex generators outlets.

FIG. 4B is a side, sectional view of the vortex generators according to the present invention, illustrating the overlapping apexes of first and second pyramid shaped portions.

DETAILED DESCRIPTION OF THE DRAWINGS

FIGS. 1–4B depict an inhaler in accordance with the principles of the invention. The inhaler includes a housing 12 which has a receptacle portion 14 connected to a conduit 16. The canister 18 forms no part of the present invention. The inhaler apparatus of the present invention is usable with any standard pressurized canister having an internal metering valve with a hollow discharge stem which may be depressed inwardly with respect to the canister body from an inoperative position in which discharge of medication is prevented, to an operative position in which a metered volume of the canister contents is discharged through the hollow discharge stem.

The conduit 16 includes an open end 20 spaced from the receptacle portion 14, and a closed end defined by an end wall 24 which is connected to the receptacle portion 14. The end wall 24 preferably is generally conical or hemispherical in shape, with an apex of the end wall 24 forming the portion of the end wall 24 farthest from the open end 20.

The inhaler 10 also includes a separate mouthpiece 60 which connects to the open end 20 of the conduit 16. The mouthpiece 60 has a reduced diameter portion 63 adapted to be inserted into the mouth of a user. The mouthpiece 60 also includes an air tube 34, having an outlet 36 spaced downstream of and in opposing relationship with the nozzle discharge orifice 30, and an air inlet 38 located on the outside of the mouthpiece. The air inlet 38 is in fluid communication with the outlet 36 of the air tube 34, providing ambient outside air to impinge on a plume of medication discharged from the orifice 30.

The housing 12 further includes an actuator and nozzle assembly 26 supported by the end wall 24. The actuator and nozzle assembly 26 includes a bore 28 which is adapted to receive the hollow discharge stem of the canister 18, and a nozzle discharge orifice 30 in fluid communication with the bore 28. The nozzle discharge orifice 30 is advantageously located at the apex of the end wall 24 and oriented to direct an aerosol plume generally along the central longitudinal axis 32 of the conduit. The orifice 30 preferably has an internal diameter at the exit of less than about 0.025 inch, and more preferably between about 0.005 inch and about 0.019 inch.

The housing 12 may be formed in three sections as shown in FIG. 1. However, for ease of manufacturing, the housing 12 may alternatively be formed in fewer than three sections. For example, the housing 12 may be formed in two sections, a first section including the receptacle portion 14, end wall 24, and the conduit 16, and a second section including the mouthpiece 60. Alternatively, the housing 14 may be formed in two split sections, split on a longitudinal plane through the conduit, where the two sections being generally mirror images of each other and are joined together along the plane of symmetry. Nevertheless, for illustration purposes, an embodiment having three sections is shown and described.

A first section 70 includes the receptacle portion 14, the end wall 24 and actuator and nozzle assembly 26, and a generally cylindrical portion 62 which forms a part of the conduit 16 and is connected to the end wall 24 at the juncture 48. The first section 70 advantageously is integrally formed of one piece, although it may alternatively be formed in multiple pieces which are subsequently joined together.

A second section 72 includes a second generally cylindrical portion whose inner and outer diameters are less than those of the first generally cylindrical section 70. The reduced diameter allows the second section to be received within the open end of the first section at the juncture 48. Second section 72 preferably is integrally formed in one piece, although it may alternatively be formed in multiple pieces which are subsequently joined.

A third section 74 of the housing 12 includes the mouthpiece 60, which is generally cylindrical and receives the other end (open end 20) of the second section 72, and also includes the air tube 34 with corresponding air inlet 36 located on the outer surface of the MDI device and the outlet 38 which provides the impinging jet.

Although the present invention is illustrated having a second section with a diameter less than that of the first section and the third section (mouthpiece), any design that allows for the connection of the sections may be used.

The housing 12 advantageously is formed of a plastic such as polyamide, polyester, polypropylene, polyethylene, ABS, polycarbonate, or polyacrylate. The housing 12 may be manufactured by any suitable technique such as injection molding or blow molding.

The inhaler 10 also includes a plurality of vortex generators within the wall of the conduit adjacent the juncture between the end wall and the conduit, and more preferably, on the end wall adjacent the juncture. Each vortex generator includes a first pyramid shaped portion 56 having an open base 58 forming an outlet on the inner surface of the conduit/end wall, and having an apex which is in fluid communication with a corresponding auxiliary ambient air inlet 46. The auxiliary air inlets 46 may be positioned on the outer surface of the end wall 24, circumferentially spaced therearound, and preferably located adjacent the juncture 48.

Preferably, the vortex generators also include a second pyramid shape, substantially similar to the first pyramid shape, having an open base in fluid communication with the auxiliary air inlets (or forming the auxiliary air inlets). The second pyramid portion includes an apex which overlaps the apex of the first pyramid portion, establishing fluid communication and creating overlapping portion 54 between the pyramid portions.

The pyramid shapes of the vortex generators yield an air flow 61 having radial and axial components relative to the conduit, establishing a circumferential-swirling, turbulent boundary layer along the inside of the conduit. This boundary layer primarily reduces the likelihood of medication particles impacting and permanently sticking to the inner walls of the conduit, and also aids in mixing air with the medication, evaporating the aerosol propellent, and directing the air/medication mixture to the mouthpiece.

Each pyramid shape includes one side at a 90 degree angle to the bottom surface. Using two pyramid shapes for the vortex generators, the apexes of the pyramids are formed together on the 90 degree sides to create an overlap (a shut-off), establishing an opening between the two pyramid shapes. The size of the opening can be varied by increasing or decreasing the apex overlap between the two pyramids. The larger the overlap, the larger the opening. Ultimately, the size of the opening determines the amount of air flow over the vortex generators. Thus, controlling the overlap determines the amount of auxiliary air flow in the boundary layer around the inner surface of the conduit.

The inhaler according to the present invention is operated as follows. A user first completely exhales and then inserts the portion 62 into the mouth with the lips closed around the portion 62, and then begins to inhale, establishing air flow from the air tube 34 and establishing the circumferential-swirling, turbulent air flow 61 from the vortex generators 54. Once these air flows are established and while continuing to inhale, the user depresses the canister 18 to discharge a metered volume of medication and propellant mixture from the nozzle discharge orifice 30. The air flowing from the air tube 34 impinges on the plume of aerosolized medication exiting the exit orifice at the apex of the end wall, slowing it down and evaporating most of the aerosol propellent. The air flow 61 generated by the vortex generators primarily keeps the inner conduit walls free of medication particles while also promoting mixing of the medication with air and evaporating the remainder of the propellant not evaporated by the impinging jet of air from the air tube 34. The user continues to inhale to fill the lungs to their capacity, and then typically holds the breath for a period of time to allow the aerosolized medication to settle within the airways of the lungs.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. An aerosol flow control apparatus comprising:
   a. a housing including an open end and a generally tubular conduit having a wall including an inner surface;
   b. a medication dispenser disposed within said housing and adapted to dispense a dose of aerosolized medication into said conduit; and
   c. a plurality of vortex generators positioned within said wall and downstream from said medication dispenser, said vortex generators having a plurality of inlets in fluid communication with ambient outside air and having a plurality of outlets located on said inner surface, wherein said vortex generators are substantially pyramid-shaped having an open base forming said outlet and having an apex in fluid communication with said air inlets and said vortex generators establishing a circumferential-swirling turbulent air flow along said inner surface upon an air flow being established through said open end.

2. The aerosol flow control apparatus according to claim 1, wherein each said vortex generator comprises a first generally pyramid-like portion having an apex and an open base forming said outlet and a second generally pyramid-like portion having an apex and an open base in fluid communication with a corresponding air inlet, said apexes overlapping to form an opening allowing fluid communication between said portions.

3. The aerosol flow control apparatus of claim 1, wherein said medication dispenser includes a pressurized canister containing medication, and said housing includes an actuator and nozzle assembly adapted to receive a hollow discharge stem of said canister, said actuator and nozzle assembly having a nozzle discharge orifice disposed to discharge aerosolized medication into said conduit.

4. The aerosol flow control apparatus of claim 1, further comprising an air tube supported within said conduit and having an outlet arranged opposite said nozzle discharge orifice and an inlet in fluid communication with ambient air outside said conduit, wherein an inspiratory effort exerted on the open end of said conduit causes air to flow into said air tube inlet and out of said air tube outlet, said air tube being oriented so that air flowing out of said air tube outlet is directed so as to impinge on a plume of aerosolized medication discharged from the canister through the nozzle discharge orifice.

5. The aerosol flow control apparatus according to claim 1, wherein said conduit includes a substantially closed end remote from said open end, said closed end including said plurality of air inlets.

6. An aerosol flow control apparatus comprising:
   a. a housing comprising a conduit defined by a wall including an inner and an outer surface, an open end adapted to be inserted into the mouth of a user and a substantially closed end remote from said open end;
   b. a medication dispenser supported in said housing and adapted to dispense a dose of aerosolized medication into said conduit;
   c. a plurality of air inlets positioned on said outer surface of said conduit; and
   d. a plurality of vortex generators positioned within said wall downstream of said medication dispenser and having a plurality of corresponding outlets located on said inner surface, said vortex generators in fluid communication with said air inlets, wherein each said vortex generator is substantially pyramid-shaped having an open base forming said outlet and having an apex in fluid communication with a corresponding air inlet wherein an inspiratory effort exerted on the open end of said conduit causes air to flow over said vortex generators establishing a circumferential-swirling turbulent boundary layer flow along the inner surface of said conduit to reduce impaction and sticking of medication thereon.

7. The aerosol flow control apparatus according to claim 6, wherein each said vortex generator comprises a first generally pyramid-like portion having an apex and an open base forming said outlet and a second generally pyramid-like portion having an apex and an open base in fluid communication with a corresponding air inlet, said apexes overlapping to form an opening allowing fluid communication between said portions.

8. The aerosol flow control apparatus of claim 6, wherein the medication dispenser comprises a pressurized canister of medication, an actuator and nozzle assembly including a bore adapted to receive a hollow outlet stem of said canister, and a nozzle discharge orifice in fluid communication with said bore and arranged to direct a plume of aerosolized medication into said conduit.

9. The aerosol flow control apparatus according to claim 6, further comprising an air tube supported within the conduit and having an outlet arranged opposite said nozzle discharge orifice and an inlet in fluid communication with ambient air outside said conduit, wherein an inspiratory effort exerted on said open end of said conduit causes air to flow into said air tube inlet and out of said air tube outlet, said air tube being oriented so that air flowing out of said air tube outlet is directed to impinge on a plume of aerosolized medication discharged from said canister through said nozzle discharge orifice.

10. The aerosol flow control apparatus of claim 6, wherein the closed end is generally conical or hemispherical in shape with an apex forming a portion of said closed end farthest from said open end of said conduit, and wherein said air inlets are positioned adjacent the juncture between said closed end and said conduit.

11. The aerosol flow control apparatus of claim 10, wherein said actuator and nozzle assembly includes a second nozzle discharge orifice in fluid communication with said bore, said two nozzle discharge orifices being spaced apart and oriented at an angle to one another such that the plumes discharged from said orifices impinge on one another within said conduit so as to promote dispersion and mixing of the aerosolized medication.

12. A method for delivering a dose of medication in an aerosol flow control apparatus comprising a housing having a conduit including an inner and an outer surface, an open end adapted to be inserted into the mouth of a user, a substantially closed end remote from said open end, and a medication dispenser supported in said housing and adapted to dispense a dose of aerosolized medication into said conduit, said method comprising the steps of:
   a. discharging a dose of medication from said medication dispenser to form a plume of aerosolized medication within said conduit; and
   b. at least during said discharging step, providing an air flow along said inner surface of said conduit by an inspiratory effort exerted on said open end of said conduit, said air flow being drawn through a plurality of air inlets formed on said outer surface of said conduit adjacent the juncture between said conduit and said closed end of said housing and over a plurality of substantially pyramid-shaped vortex generators having an open base forming said outlet and having an apex in fluid communication with said air inlets formed within said wall downstream of said medication dispenser and having said outlets adjacent said inner surface of said conduit, wherein a circumferential-swirling turbulent boundary layer flow is created along said inner surface of said conduit to reduce impaction and adhesion of medication thereon.

13. An aerosol flow control apparatus comprising:
   a. a housing including an open end and a generally tubular conduit, said conduit having a wall including an inner surface, a plurality of air inlets in fluid communication with ambient outside air;
   b. a medication dispenser disposed within said housing and adapted to dispense a dose of aerosolized medication into said conduit; and
   c. a plurality of vortex generators positioned within said wall of said conduit downstream of said medication dispenser, wherein each said vortex generator comprises a first generally pyramid-like portion having an apex and an open base forming an outlet located on said inner surface and a second generally pyramid-like portion having an apex and an open base in fluid communication with a corresponding air inlet, said apexes overlapping to form an opening allowing fluid communication between said pyramid-like portions, and wherein said vortex generators and said air inlets cooperate to establish a circumferential-swirling turbulent air flow along said inner surface upon an air flow being established through said open end.

* * * * *

UNITED STATES PATENT AND TRADEMARK OFFICE
CERTIFICATE OF CORRECTION

PATENT NO.    : 6,367,471 B1
DATED         : April 9, 2002
INVENTOR(S)   : Amir Genosar et al.

It is certified that error appears in the above-identified patent and that said Letters Patent is hereby corrected as shown below:

Column 3,
Line 37, "non" should read -- on --.

Column 4,
Line 1, "section" should read -- sectional --; and
Line 56, "housing 14" should read -- housing 12 --.

Column 6,
Line 10, "propellent." should read -- propellant. --;

Signed and Sealed this

Fifteenth Day of April, 2003

JAMES E. ROGAN
*Director of the United States Patent and Trademark Office*